US009927097B2

United States Patent
Lalicki et al.

(10) Patent No.: US 9,927,097 B2
(45) Date of Patent: Mar. 27, 2018

(54) SINGLE DIODE DISINFECTION

(71) Applicant: Vital Vio, Inc., Troy, NY (US)

(72) Inventors: Jorel Lalicki, Troy, NY (US); Robert Barron, Troy, NY (US); James W Peterson, Troy, NY (US)

(73) Assignee: Vital Vio Inc., Troy, NY (US)

( * ) Notice: Subject to any disclaimer, the term of this patent is extended or adjusted under 35 U.S.C. 154(b) by 0 days.

(21) Appl. No.: 15/223,134

(22) Filed: Jul. 29, 2016

(65) Prior Publication Data

US 2017/0030555 A1    Feb. 2, 2017

Related U.S. Application Data

(60) Provisional application No. 62/198,726, filed on Jul. 30, 2015.

(51) Int. Cl.
*A61L 2/08* (2006.01)
*F21V 9/16* (2006.01)
(Continued)

(52) U.S. Cl.
CPC ............ *F21V 9/16* (2013.01); *A61L 2/084* (2013.01); *F21K 9/64* (2016.08); *H01L 33/502* (2013.01);
(Continued)

(58) Field of Classification Search
CPC .................................. A61L 2/084; F21V 9/16
(Continued)

(56) References Cited

U.S. PATENT DOCUMENTS 3,670,193 A   6/1972  Thorington et al.
3,992,646 A   11/1976 Garth
(Continued)

FOREIGN PATENT DOCUMENTS

EP    1693016 A1    8/2006
EP    1887298 A1    2/2008
(Continued)

OTHER PUBLICATIONS

Dai et al., "Blue light for infectious diseases: Propionibacterium acnes, Helicobacter pylon, and beyond?," Drug Resist Updat., 15(4): 223-236 (Aug. 2012).
(Continued)

*Primary Examiner* — Christopher Raabe
(74) *Attorney, Agent, or Firm* — Hoffman Warnick LLC

(57) ABSTRACT

Disclosed herein is a device which inactivates microorganisms. The device includes a light emitter and at least one light-converting material arranged to convert at least a portion of light from the light emitter. Any light emitted from the light emitter and converted light emitted from the at least one light-converting material mixes to form a combined light, the combined light having a proportion of spectral energy measured in an approximately 380 nm to approximately 420 nm range of greater than approximately 20 percent. In another embodiment, the device includes a light emitter configured to emit light with wavelengths in a range of 380 to 420 nm, and at least one light-converting material including at least one optical brightener and configured to emit a second light. The first light exiting the device and the second light exiting the device mix to form a combined light, the combined light being white.

20 Claims, 6 Drawing Sheets

(51) Int. Cl.
*F21K 9/64* (2016.01)
*H01L 33/50* (2010.01)
*F21Y 115/10* (2016.01)
*H01L 33/52* (2010.01)

(52) U.S. Cl.
CPC ........ *A61L 2202/11* (2013.01); *F21Y 2115/10* (2016.08); *H01L 33/52* (2013.01)

(58) Field of Classification Search
USPC .......................................................... 313/501
See application file for complete search history.

(56) References Cited

U.S. PATENT DOCUMENTS

| | | | |
|---|---|---|---|
| 6,242,752 | B1 | 6/2001 | Soma et al. |
| 6,791,259 | B1 | 9/2004 | Stokes et al. |
| 7,658,891 | B1 | 2/2010 | Barnes |
| 8,398,264 | B2 | 3/2013 | Anderson et al. |
| 8,476,844 | B2 | 7/2013 | Hancock et al. |
| 8,508,204 | B2 | 8/2013 | Deurenberg et al. |
| 9,039,966 | B2 † | 5/2015 | Anderson |
| 9,046,227 | B2 † | 6/2015 | David |
| 9,333,274 | B2 * | 5/2016 | Peterson ................. A61L 2/084 |
| 9,368,695 | B2 † | 6/2016 | David |
| 9,410,664 | B2 | 8/2016 | Krames et al. |
| 9,439,989 | B2 * | 9/2016 | Lalicki ...................... A61L 2/08 |
| 9,581,310 | B2 | 2/2017 | Wu et al. |
| 2003/0124023 | A1 | 7/2003 | Burgess et al. |
| 2004/0008523 | A1 | 1/2004 | Butler |
| 2005/0055070 | A1 | 3/2005 | Jones et al. |
| 2005/0207159 | A1 | 9/2005 | Maxik |
| 2006/0022582 | A1 | 2/2006 | Radkov |
| 2006/0071589 | A1 * | 4/2006 | Radkov .............. C09K 11/0883 313/487 |
| 2006/0186377 | A1 | 8/2006 | Takahashi et al. |
| 2006/0262545 | A1 | 11/2006 | Piepgras et al. |
| 2008/0008620 | A1 | 1/2008 | Alexiadis |
| 2008/0278927 | A1 | 11/2008 | Li et al. |
| 2008/0305004 | A1 | 12/2008 | Anderson et al. |
| 2009/0034236 | A1 | 2/2009 | Reuben |
| 2009/0231832 | A1 | 9/2009 | Zukauskas et al. |
| 2010/0001648 | A1 | 1/2010 | De Clercq et al. |
| 2010/0121420 | A1 | 5/2010 | Fiset et al. |
| 2010/0232135 | A1 | 9/2010 | Munehiro et al. |
| 2010/0246169 | A1 | 9/2010 | Anderson et al. |
| 2012/0281408 | A1 | 11/2012 | Owen et al. |
| 2012/0320607 | A1 | 12/2012 | Kinomoto et al. |
| 2013/0077299 | A1 | 3/2013 | Hussell et al. |
| 2013/0313516 | A1 | 11/2013 | David et al. |
| 2013/0313546 | A1 | 11/2013 | Yu |
| 2014/0254131 | A1 | 9/2014 | Osinski et al. |
| 2014/0328046 | A1 | 11/2014 | Aanegola et al. |
| 2015/0129781 | A1 | 5/2015 | Kretschmann |
| 2015/0182646 | A1 | 7/2015 | Anderson et al. |
| 2016/0015840 | A1 | 1/2016 | Gordon |
| 2016/0030610 | A1 | 2/2016 | Peterson et al. |
| 2016/0271281 | A1 | 9/2016 | Clynne et al. |
| 2016/0273717 | A1 | 9/2016 | Krames et al. |
| 2016/0276550 | A1 | 9/2016 | David et al. |
| 2016/0375161 | A1 | 12/2016 | Hawkins et al. |
| 2016/0375162 | A1 | 12/2016 | Marry et al. |
| 2016/0375163 | A1 | 12/2016 | Hawkins et al. |
| 2017/0014538 | A1 | 1/2017 | Rantala |

FOREIGN PATENT DOCUMENTS

| | | | |
|---|---|---|---|
| EP | 1943880 | B1 | 4/2013 |
| JP | 2003339845 | A | 12/2003 |
| WO | 0114012 | A1 | 3/2001 |
| WO | 03063902 | A2 | 8/2003 |
| WO | 2004033028 | A2 | 4/2004 |
| WO | 2006100303 | A2 | 9/2006 |
| WO | 2006126482 | A1 | 11/2006 |
| WO | 2007012875 | A1 | 2/2007 |
| WO | 2009056838 | A1 | 5/2009 |
| WO | 2015066099 | A2 | 5/2015 |
| WO | 2016019029 | A1 | 2/2016 |

OTHER PUBLICATIONS

Halstead et al., "The antibacterial activity of blue light against nosocomial wound pathogens growing planktonically and as mature biofilms," Appl. Environ, Microbiol., Apr. 2016, 38 pages, retrieved from: http://aem.asm.org/.

R.S. McDonald et al., "405 nm Light Exposure of Osteoblasts and Inactivation of Bacterial Isolates From Arthroplasty Patients: Potential for New Disinfection Applications?," European Cells and Materials vol. 25, (2013), pp. 204-214.

Tomb et al., "Inactivation of Streptomyces phage φ C31 by 405 nm light," Bacteriophage, 4:3, Jul. 2014, retrieved from: http://dx.doi.org/10.4161/bact.32129, 7 pages.

Tsukada et al., "Bactericidal Action of Photo-Irradiated Aqueous Extracts from the Residue of Crushed Grapes from Winemaking," Biocontrol Science, vol. 21, No. 2, (2016), pp. 113-121, retrieved from: https://www.researchgate.net/publication/304628914.

International Search Report and Written Opinion issued in connection with corresponding PCT Application No. PCT/US2016/036704 dated Dec. 8, 2016, 20 pages.

LEDs Magazine, "Lumination Vio LED combines 405 nm chip with new phosphors," retrieved from the Internet on Apr. 20, 2017 at: http://www.leds.magazine.com/articles/2007/06/lumination-vio-led-combines-405-nm-chip-with-new-phosphors.html, Published Jun. 14, 2007, 2 pages.

LEDs Magazine, "ANSI evaluates revisions to SSL chromaticity standard," retrieved from the Internet on Apr. 20, 2017 at: http://www.ledsmagazine.com/articles/2011/07/ansi-evaluates-revisions-to-ssl-chromaticity-standard-magazine.html, Published Jul. 18, 2011, 4 pages.

LEDs Magazine, "ANSI works to update the solid-state lighting standard for chromaticity," retrieved from the Internet on Apr. 20, 2017 at: http://www.ledsmagazine.com/articles/print/volume-12/issue-2/features/standards/ansi-works-to-Update-the-ssl-chromaticity-standard.html, Published Feb. 23, 2015, 5 pages.

LEDs Magazine, "ANSI continues advancements on SSL chromaticity standard," retrieved from the Internet on Apr. 20, 2017 at: http://www.ledsmagazine.com/articles/print/volume-12/issue-11/features/standards/ansi-continues-advancements-on-ssl-chromaticity-standard.html, Published Dec. 8, 2015, 6 pages.

Soraa, "PAR30L," retrieved from the Internet on Apr. 20, 2017 at: http://www.soraa.com/products/22-PAR30L, 5 pages.

Soraa, "PAR30L 18.5W," retrieved from the Internet on Apr. 20, 2017 at: http://www.soraa.com/products, 5 pages.

Bache et al., "Clinical studies of the High-Intensity Narrow-Spectrum light Environmental Decontamination System (HINS-light EDS), for continuous disinfection in the burn unit inpatient and outpatient settings," Burns 38 (2012), pp. 69-76.

Patent Cooperation Treaty, Search Report—Written Opinion, International Application No. PCT/US16/44634, dated Oct. 20, 2016, 14 pages.

Color Phenomena, "CIE-1931 Chromaticity Diagram," last updated Aug. 22, 2013, retrieved from www.color-theory-phenomena.nl/10.02.htm on Jan. 20, 2016, 3 pages.

Patent Cooperation Treaty, Written Opinion of the International Searching Authority and International Search Report for PCT/US2015/042678 dated Nov. 2, 2015, 13 pages.

Patent Cooperation Treaty, International Preliminary Report on Patentability for PCT/GB2008/003679 dated May 4, 2010, 9 pages.

Patent Cooperation Treaty, Written Opinion of the International Searching Authority and International Search Report for PCT/GB2008/003679 dated Oct. 31, 2008, 11 pages.

\* cited by examiner
† cited by third party

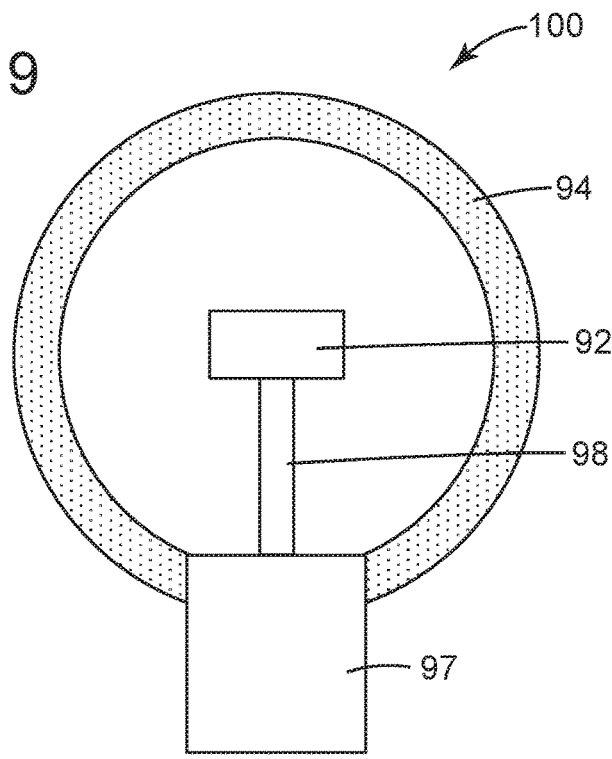
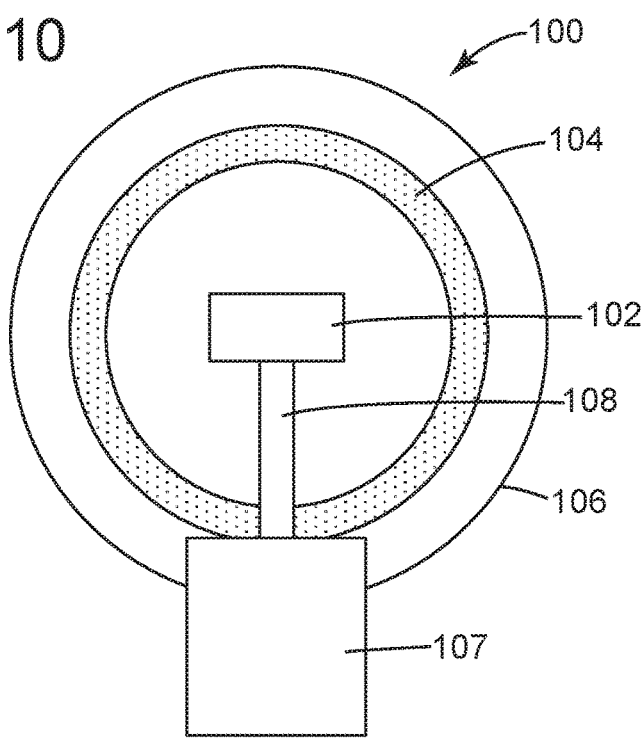

SINGLE DIODE DISINFECTION

TECHNICAL FIELD DISCLOSURE

The present disclosure concerns a light-emitting device capable of emitting light that can be perceived as white or a hue of white, and more particularly, a light emitting device capable of emitting light that can be perceived as white or a hue of white while simultaneously causing the inactivation of microorganisms.

BACKGROUND OF THE DISCLOSURE

Light-emitting devices are a primary requirement in most indoor occupied environments to provide illumination of the area, of tasks being completed in the area, and of the area's occupants and objects. Lighting technologies range widely for use indoors, from incandescent and halogen bulbs, to fluorescent and light-emitting diode (LED) bulbs and devices, among many other technologies. The primary purpose of these lighting technologies to date is to provide light that can be observed by humans as what is considered "white" light, which can effectively illuminate different colors, textures, and features of objects in a manner pleasing to humans.

While many technologies are commercially used in lighting, LED lighting is growing as a technology to provide efficient, high quality white light illumination at an effective cost point. Some common LEDs for general illumination use a semiconductor junction that is energized to emit blue light and that is combined with a phosphor material, such as cerium-doped yttrium aluminum garnet (YAG:Ce) to convert a portion of that blue light to other wavelengths of light, such as yellow wavelengths. When balanced properly, the combined light emitted from the semiconductor junction and the phosphor material is perceived as white or a hue of white. Blue light-emitting semiconductors are used currently for many reasons, including relatively high efficiency, relatively low cost, and relatively desirable color benefits of the blue light contribution to the overall spectrum of light (as compared to light-emitting semiconductors that emit light of another color).

Some alternative LED technologies use semiconductor junctions that emit UV, near UV, or violet light instead of blue light. A phosphor material is combined to convert a portion of the blue, violet, or UV light to other wavelengths of light and the two components are balanced appropriately to provide white or a hue of white light. Violet LEDs are used less frequently due to typically lower efficiency and cost performance, but have commercially been shown to be able to provide an adequate visual quality of light in some characteristics like the Color Rendering Index (CRI).

With both of these LED technologies, achieving a relatively high luminous efficacy of emitted radiation is balanced against achieving desirable color characteristics (CRI, correlated color temperature (CCT), Gamut, etc.) of the emitted radiation. In other words, the wavelength of combined light emitted from the lighting device is chosen, in relation to the spectral sensitivity of the human eye, to achieve high efficiency, while minimizing the sacrifice of desired color characteristics.

Alternative light sources have been created with additional performance factors in mind that utilize emitted light in different manners. Lighting fixtures and devices for horticulture, health, warmth, and disinfection have been demonstrated. In addition to being tuned for luminous efficacy of radiation, these lighting fixtures and devices are tuned to provide increased outputs of certain regions of radiation to accomplish the additional performance factor.

These lighting fixtures and devices provide a dual or multiple function of lighting through the use of various alternative functions of light such as photochemical, photobiological, radiant energy, and others. Typically, radiant energy outputs are attempted to be optimized for specific regions matching absorption or activation spectrums of the added function. For example, light fixtures and devices for horticulture are attempted to be optimized for emitting light matching absorption or activation spectrums of chlorophyll and other plant based photo-activated mechanisms. Light fixtures and devices for assisting circadian rhythm are attempted to be optimized for emitting light matching absorption or activation spectrums of melatonin.

In these lighting fixtures and devices that emit light for multiple functions, the light emissions can be balanced to achieve an acceptable level of each function. One of the functions can be general illumination (e.g., when the multiple-function lighting fixtures and devices are used in spaces occupied by humans), in which case, achieving a relatively high luminous efficacy of the emitted light is balanced not only against achieving desirable color characteristics of the emitted light, but also of achieving the one or more other functions to an acceptable or desired level.

BRIEF DESCRIPTION OF THE DISCLOSURE

Embodiments of the disclosure disclosed herein may include a device which inactivates microorganisms, the device including a light emitter and at least one light converting material arranged to convert at least a portion of light from the light emitter, wherein any light emitted from the light emitter and the at least a portion of converted light emitted from the at least one light-converting material mixes to form a combined light, the combined light having a proportion of spectral energy measured in an approximately 380 nm to approximately 420 nm wavelength range of greater than approximately 20%.

Embodiments of the disclosure herein may include a device which inactivates microorganisms, the device including a light emitter and at least one light-converting material arranged to be in a direct path of the first light. The light emitter is configured to emit a first light within a range of 380 nm to 420 nm, and the at least one light-converting material is configured to emit a second light in response to the first light being incident on the at least one light-converting material. The first light exiting the device and the second light exiting the device mix to form a combined light, the combined light being white. The at least one light-converting material includes at least one optical brightener which emits light in the wavelength range of 450 nm to 495 nm.

BRIEF DESCRIPTION OF THE DRAWINGS

These and other features of the disclosure will be more readily understood from the following detailed description of the various aspects of the disclosure taken in conjunction with the accompanying drawings that depict various aspects of the disclosure.

FIG. 9 illustrates another light-emitting device according to various embodiments.

FIG. 10 illustrates another light-emitting device according to various embodiments.

Figure 1:
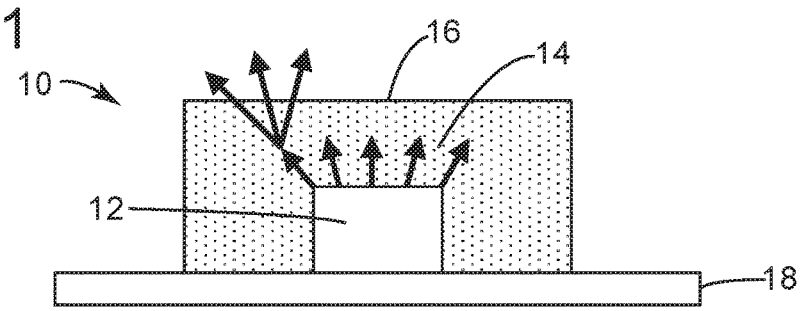
FIG. 1 illustrates a light-emitting device according to various embodiments.

It is noted that the drawings may not be to scale. The drawings are intended to depict only typical aspects of the disclosure, and therefore should not be considered as limiting the scope of the disclosure. In the drawings, like numbering represents like elements between the drawings. The detailed description explains embodiments of the disclosure, together with advantages and features, by way of example with reference to the drawings.

DETAILED DESCRIPTION OF THE DISCLOSURE

According to various embodiments, a lighting device is disclosed that is capable of emitting light that can be perceived as white or a hue of white and simultaneously is capable of emitting certain concentrations of light with specific wavelengths that are associated with the inactivation of at least some microorganisms. The light-emitting device is composed of a light emitter (e.g., LEDs, lasers) and one or more light-converting materials (e.g., phosphors, optical brighteners) assembled in a manner that light emitted from light emitter will be directed into the light-converting material(s) and at least a portion of this light directed into the light-converting material(s) will be converted by the light-converting material(s) to light having a different quality (e.g., a different peak wavelength). Light can be converted by the light-converting material(s) by absorbing the light, which energizes or activates the light-converting material(s) to emit light of a different quality (e.g., a different peak wavelength). A combined light emitted by the light emitter and the light-converting material(s) has a proportion of spectral energy measured in an approximately 380 nm to approximately 420 nm wavelength range of greater than approximately 20%.

The light emitter and light-converting material(s) may be assembled in many different manners, such as, but not limited to the embodiments depicted in FIGS. 1-15. Light emitted by the light emitter(s) and the light-converting material(s) can be modified by optics, reflectors, or other assembly components to facilitate the combined light emitted by the light-emitting device being perceived as white or a hue of white. Referring to FIG. 1, a light-emitting device 10 is illustrated that includes a pump LED 12 as the light emitter, a light-converting material 14, an encapsulant 16, and a substrate 18. The light-converting material 14 may be dispersed within encapsulant 16. Pump LED 12 and light-conversion material 14 are supported on the substrate 18.

Figure 2:
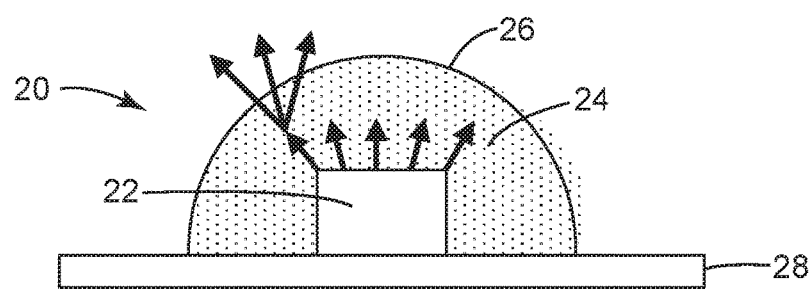
FIG. 2 illustrates another light-emitting device according to various embodiments.

FIG. 2 illustrates a light-emitting device 20 that includes a packaged pump LED 22 as the light emitter, a light-converting material 24, a lens 26 containing the light-converting material 24, and a substrate or base 28.

Figure 3:
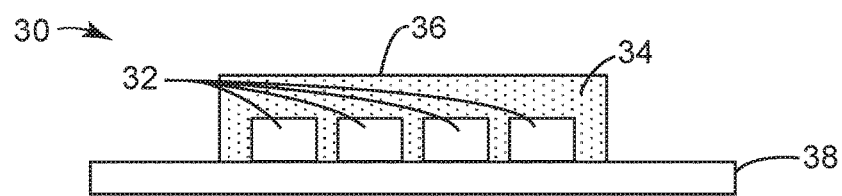
FIG. 3 illustrates another light-emitting device according to various embodiments.

FIG. 3 illustrates a light-emitting device 30 that includes an array of pump LEDs 32 contained by a light-converting material 34 that is evenly distributed within an encapsulant 36.

Figure 4:
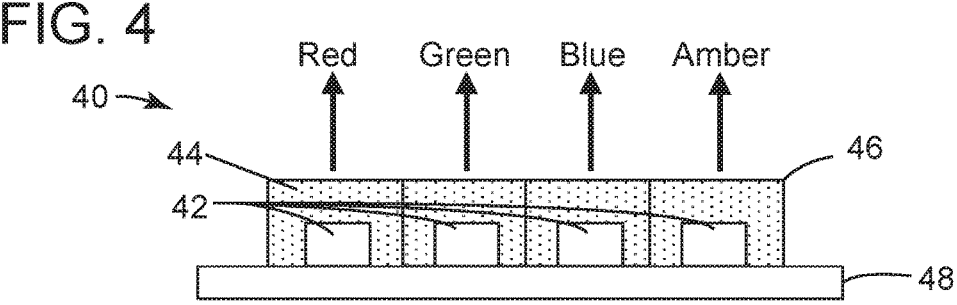
FIG. 4 illustrates another light-emitting device according to various embodiments.

FIG. 4 illustrates a light-emitting device 40 that includes an array of LEDs 42 with light-converting materials 44 that convert light to red, green, blue, and amber light. The light-converting materials 44 are shown dispersed, or contained, in an encapsulant 46. LEDs 42 and encapsulant 46 are shown supported on a substrate 48.

Figure 5:
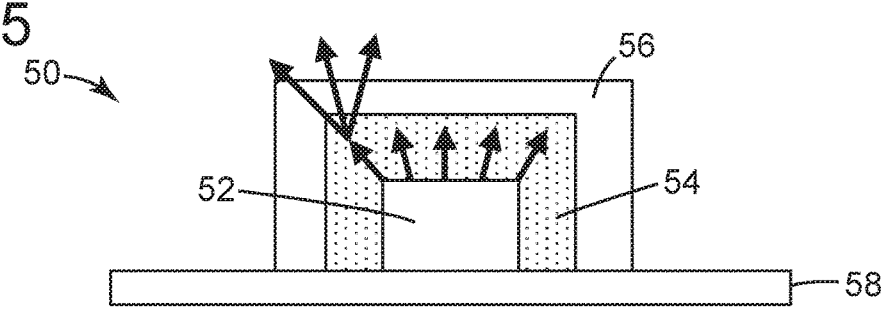
FIG. 5 illustrates another light-emitting device according to various embodiments.

FIG. 5 illustrates a light-emitting device 50 that includes LED 52 contained by a light-converting material 54 that is contained by an encapsulant 56, all of which is supported on a substrate 58.

Figure 6:
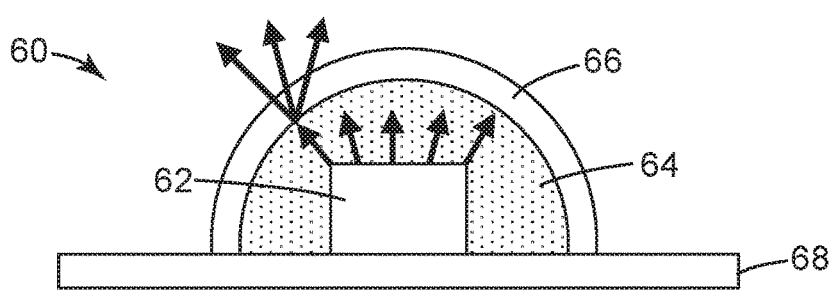
FIG. 6 illustrates another light-emitting device according to various embodiments.

FIG. 6 illustrates a light-emitting device 60 that includes a packaged LED 62 contained by a light-converting material 64 that is contained by a lens 66. LED 62, light-converting material 64, and lens 66 are supported by a base or substrate 68.

Figure 7:
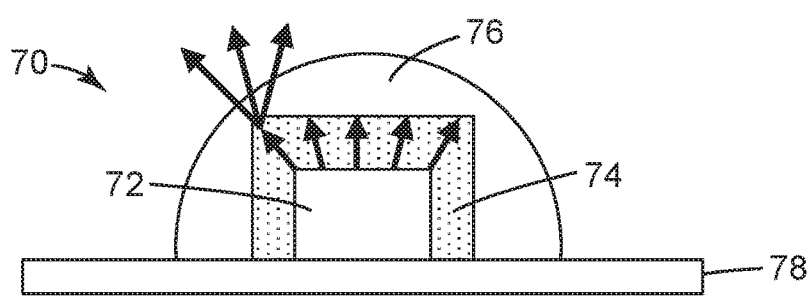
FIG. 7 illustrates another light-emitting device according to various embodiments.

FIG. 7 illustrates a light-emitting device 70 that includes a packaged LED 72 contained by conformally coated light-converting material 74 that is contained by a lens 76. LED 72, light-converting material 74, and lens 76 are supported on a base or substrate 78.

Figure 8:
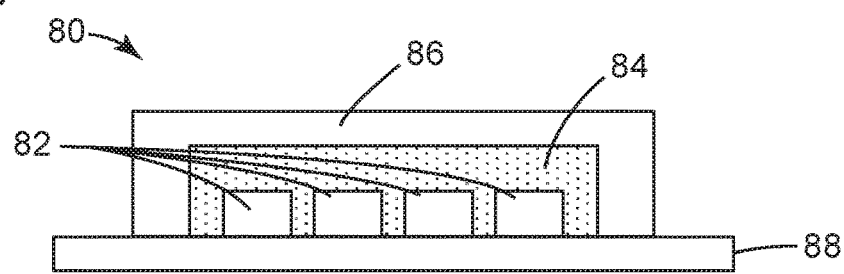
FIG. 8 illustrates another light-emitting device according to various embodiments.

FIG. 8 illustrates a light-emitting device 80 that includes an array of LEDs 82 contained by a light converting-material 84 that is contained by an encapsulant 86. LEDs 82, light-converting material 84, and encapsulant 86 are supported on a substrate 88.

FIG. 9 illustrates a light-emitting device 90 that is a light bulb including LED 92, an outer light-converting filter 94, a base 97, and a pedestal 98. Base 97 and pedestal 98 support LED 92.

FIG. 10 illustrates a light-emitting device 100 that is a light bulb including an LED 102, a light-converting filter 104 contained by an outer bulb 106, a base 107, and a pedestal 108. Light-converting filter 104 can directly contact outer bulb 106.

Figure 11:
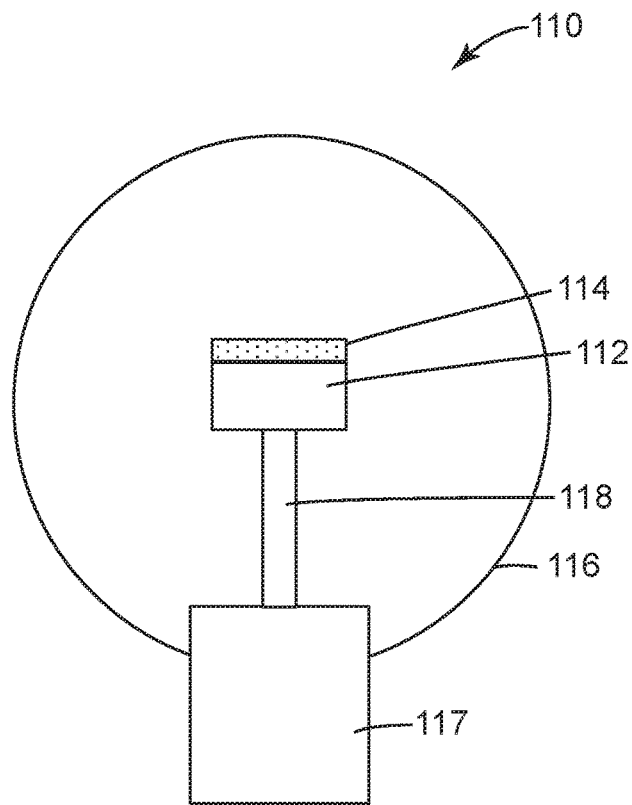
FIG. 11 illustrates another light-emitting device according to various embodiments.

FIG. 11 illustrates a light-emitting device 110 that is a light bulb including an LED 112, a light-converting filter 114 on top of the pump LED 112, an outer bulb 116, a base 117, and a pedestal 118. Light-converting filter 114 can be directly on the pump LED 112.

Figure 12:
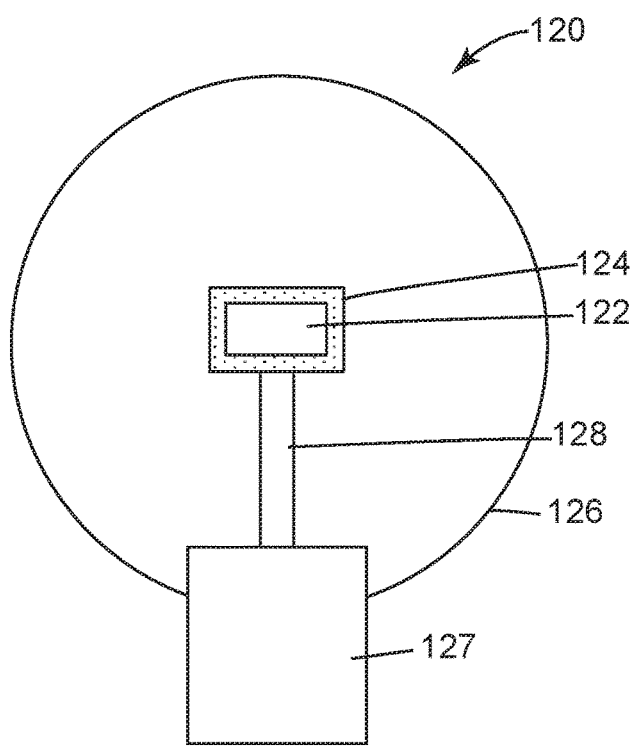
FIG. 12 illustrates another light-emitting device according to various embodiments.

FIG. 12 illustrates a light-emitting device 120 that is a light bulb including an LED 122, a light-converting filter 124 surrounding the pump LED 122, an outer bulb 126, a base 127, and a pedestal 128. Light-converting filter 124 can directly contact pump LED 122.

Figure 13:
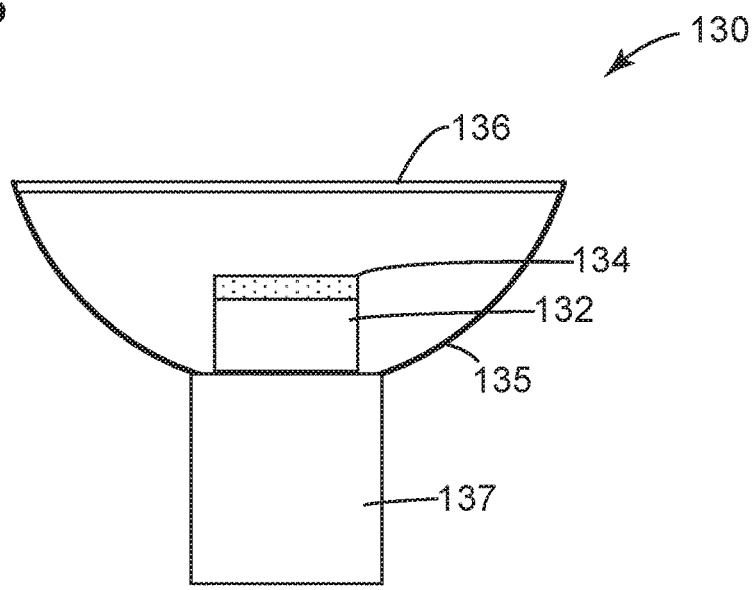
FIG. 13 illustrates another light-emitting device according to various embodiments.

FIG. 13 illustrates a light-emitting device 130 that is a spot lamp including an LED 132, a light-converting filter 134 on pump LED 132, a reflector 135, a lens 136, and a base 137. Light-converting filter 134 can be directly on pump LED 132.

Figure 14:
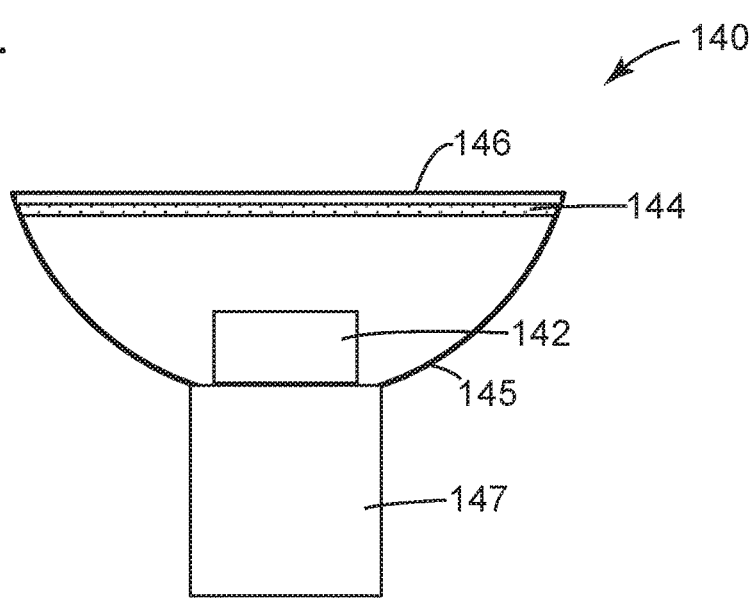
FIG. 14 illustrates another light-emitting device according to various embodiments.

FIG. 14 illustrates a light-emitting device 140 that is a spot lamp including, an LED 142, a light-converting filter 144, a reflector 145, a lens 146 on light-converting filter 144, and a base 147. Lens 146 can be directly on light-converting filter 144.

Figure 15:
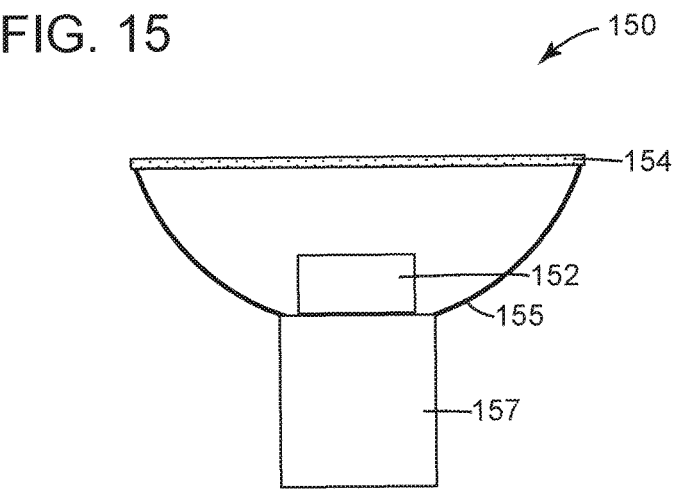
FIG. 15 illustrates another light-emitting device according to various embodiments.

FIG. 15 illustrates a light-emitting device 150 that is a spot lamp including an LED 152, a light-converting filter 154, a reflector 155, and a base 157.

Though illustrated in FIGS. 1-15 as an LED, the light emitter can be any known emitter, including but not limited to a substrate and an LED (e.g., pump LED), a packaged LED, an array of LEDs, a spot lamp, a laser, and traditional light bulbs either with an LED replacement fixture or other light bulbs. The light emitter can have a peak wavelength/majority of light output in the 380-420 nm wavelength range of light. In embodiments with multiple light emitters (e.g., an array of LEDs), the light emitters can all emit light of approximately the same wavelength. For example, the array of LEDs 32 shown in FIG. 3 and the array of LEDs 42 shown in FIG. 4 can all emit light within the range of 380-420 nm. In some embodiments, the array of LEDs 32, 42 can all emit light within the wavelength range of 390-415 nm, and in other embodiments 400 nm-410 nm.

Light-converting material, as used herein, constitutes a broad category of materials, substances, or structures that have the capability of absorbing a certain wavelength of light and re-emitting it as another wavelength of light. Light-converting materials should be noted to be different from light-emitting materials and light-transmitting/filtering materials. Light-emitting materials can be broadly classified as materials, substances, or structures/devices that convert a non UV-VIS-IR form of energy into a UV-VIS-IR light emission. Non ultraviolet-visible-infrared (UV-VIS-IR) forms of energy may be, and are not limited to: electricity, chemical reactions/potentials, microwaves, electron beams, and radioactive decay. Light-converting materials may be contained in or deposited on a medium, making a light-converting medium. It should be understood that light-converting materials, light-converting mediums, light-converting filters, phosphors, and any other terms regarding the conversion of light are meant to be examples of the light-converting material disclosed. In some embodiments, the light-converting material can be a phosphor, an optical brightener, a combination of phosphors, a combination of optical brighteners, or a combination of phosphor(s) and optical brightener(s). Optical brighteners are light-converting materials (e.g., chemical compounds) that absorb light in the ultraviolet and/or violet regions of the electromagnetic spectrum, and re-emit light in the blue region. Light-converting materials can be capable of absorbing multiple different wavelengths of light and emitting multiple different wavelengths of light, in both scaled and not specifically scaled manners.

The phosphor or other light converting material may be deposited directly on the light emitter, as illustrated in at least FIGS. 1-7, or may be remote or further removed from the light emitter, as illustrated in at least FIGS. 9-10 and 14-15, which show a light-converting filter distanced from the light emitter. The remote phosphor configuration reduces flux density through the light-converting filter by increasing surface area of the flux. The physical separation of the light emitter and the light-converting filter, and the reduced flux can reduce the operating temperature of the light-converting filter by reducing conducted heat from the light emitter. The lower temperature of the light-converting filter reduces thermal quenching of the light output and other undesirable effects of elevated operating temperature. Light-converting materials can be deposited, for example, as conformal coatings, doped encapsulants or binder materials, and remote phosphors. The at least one light-converting material may be fully homogenized at different or identical ratios and used as a bulk mix, or the at least one light-converting materials may have some or all portions positioned or layered separately, affecting the absorption and emission of different materials that may not be compatible when mixed or that may absorb too much underlying light.

In some embodiments, the CRI value of the combined light output or combined emitted light from the light-emitting device (e.g., light emitted from the light emitter mixed with light emitted from the light-conversion material) can have a CRI value of at least 55, 60, 65, or 70. In further embodiments, the CRI value can be at least 80, 85, 90, or 95, plus or minus approximately 5.

In some embodiments, the combined light output or combined emitted light from the light-emitting device can be white light. White light can be defined as light with a correlated color temperature (CCT) value of approximately 1000 kelvin (K) to approximately 8000K, in some embodiments approximately 2000K to approximately 6000K, and in some embodiments approximately 2,500K to approximately 5,000K, wherein "approximately" can include plus or minus about 200K.

In some embodiments, the light-emitting device can have a spectral content of light output in the 380-420 nm wavelength range of at least 20%. The spectral content of light output in the 380-420 nm wavelength range is defined as the proportion of absolute irradiance value of light having wavelengths in the range of 380-420 nm relative to the absolute irradiance value of light having wavelengths in the range of 380-720 nm. Dividing the former value by the latter value yields the % spectral content of emitted light in the 380-420 nm wavelength range. The spectral output is defined as the radiometric energy. The absolute irradiance values can be measured by any now-known or later-developed means. In some embodiments, the absolute irradiance values are measured in mW of radiometric energy.

The spectral content in the 380-420 nm wavelength range can be utilized for the inactivation of bacterial pathogens. A 405 nm peak wavelength and a range of wavelengths above and below 405 nm (380-420 nm) have proven effective for the inactivation of bacterial pathogens.

As one example, the device may be assembled similarly to a "blue-phosphor" LED device. A blue-phosphor LED device is a single package electronic device capable of emitting light. The embodiment of the device depicted in FIG. 2, as well as several of the other figures, for example, could be architecturally similar to a "blue-phosphor" LED device. Typically, in a "blue-phosphor" LED device, a semiconductor LED capable of emitting blue light is covered or surrounded by a phosphor material or otherwise placed so that light emitted from the diode passes though the phosphor. The "blue-phosphor" LED device emits some portion of the original blue light from the LED, and some of the light from the phosphor which has been converted from blue light. The "blue-phosphor" LED device has a combined light emission ratio of the blue light and the light emitted from the phosphor to emit a light that is overall perceived as white.

The LED device according to embodiments of the disclosure is assembled similarly to a "blue-phosphor" LED device but includes a semiconductor LED that emits a majority of light/peak of light within the 380-420 nm wavelength range rather than wavelengths within the conventional range of approximately 450-495 nm, which would be perceived as blue. Light in the 380-420 nm wavelength is capable of killing or deactivating microorganisms such as but not limited to Gram positive bacteria, Gram negative bacteria, bacterial endospores, and yeast and filamentous fungi. Some Gram positive bacteria that can be killed or deactivated include *Staphylococcus aureus* (incl. MRSA), *Clostridium perfringens, Clostridium difficile, Enterococcus faecalis, Staphylococcus epidermidis, Staphyloccocus hyicus, Streptococcus pyogenes, Listeria monocytogenes, Bacillus cereus*, and *Mycobacterium terrae*. Some, Gram negative bacteria include *Acinetobacter baumannii, Pseudomonas aeruginosa, Klebsiella pneumoniae, Proteus vulgaris, Escherichia coli, Salmonella enteritidis, Shigella sonnei*, and *Serratia* spp. Some bacterial endospores include *Bacillus cereus* and *Clostridium difficile*. Some yeast and filamentous fungi include *Aspergillus niger, Candida albicans*, and *Saccharomyces cerevisiae*. Light in the 380-420 nm wavelength has been effective against every type of bacteria tested, although it takes different amounts of time or dosages dependent on species. Based on known results it is expected to be effective against all gram-negative and gram-positive bacteria to some extent over a period of time. It can also be effective against many varieties of fungi, although these will take longer to show an effect. The LED, according to embodiments of the disclosure, is surrounded by a phosphor material capable of absorbing and converting some portion of that anti-microbial light emitted from the LED (380-420 nm) to an alternative wavelength or wavelengths. This LED device can have a combination of selected phosphors, such as but not limited to Lutetium Aluminum Garnet and Nitride, that when combined at the proper ratios can emit a light perceived as white or a hue of white. This example LED device can have a CRI equal to or greater than 70. In some embodiments, this example LED device can have a CRI equal to or greater than 80. A percentage of spectral content of light emitted from the example LED device with approximately 380-420 nm wavelength can be equal to or greater than 20%. In some embodiments, light with wavelengths in the range from approximately 380-420 nm may comprise at least approximately 25%, 30%, 35%, 40%, 45%, or 50% of the total combined light emitted from the example LED device.

In some embodiments, the light-emitting device can be a surface mount LED device, which includes an LED and a light-conversion material. The surface mount LED device can be mounted onto a printed circuit board ("PCB") or otherwise configured to be capable of transferring power to the light-emitting device and to the LED. The LED can be coupled to the PCB through bond wires or leads which enable an electrical connection from the LED to the outside of the device. The device may have a lens, encapsulant, or other protective cover. The embodiments shown in FIGS. 1-8 can be embodied as surface mount LED devices by arranging them with wires or leads connected to the respective LEDs and configured to be connected to a PCB.

In additional embodiments, the light-emitting device can be a through-hole LED device, which is similar to a surface mount package but is intended to be mounted to a PCB board or otherwise configured to be capable of transferring power into the device and the light emitter via conductive legs which mate with matched holes or vias on the PCB or similar structure. The legs are coupled to the PCB or similar structure through solder or another conductive medium.

In some embodiments, the light-emitting device can be a chip-on-board LED arrangement, which is a package with one or more light sources and a light converting-material. The one or more light sources can be mounted directly to a substrate, and the light-converting material can be placed so a desired portion of emitted light is converted by the light converting material.

Unlike previous attempts with devices to produce acceptable light spectrums, which required multiple different light emitters to be incorporated into a device to achieve white light of acceptable characteristics, embodiments of the disclosure do not require multiple different light emitters, which would each require its emitted light to be combined through optics or housing structures, which in turn would require increased electronics, controls, optics, and housing structures. The additional features and increased cost metrics associated with multiple-light-emitter light-emitting devices make color mixing methods inherently cumbersome for these light-emitting devices as compared to light-emitting devices with single light emitters, which can produce a combined light spectrum out of a single assembly.

In one embodiment, a device is disclosed which comprises a unit that uses only violet LEDs (approximately 405 nm) to create white light, while maintaining the disinfection capabilities of the desired spectrum. Color temperatures of 2700 k, 3500 k, and 4100 k, with CRI above 80 are possible with a single light emitter (e.g., LED) according to embodiments of the disclosure. Generally, a CCT range of 2700-5000 k with minimum CRI of 70, and violet spectral content above 20% is possible. In some embodiments, the use of two or more light-converting materials can achieve these values. In some embodiments, phosphors that convert light to each of red (620-750 nm), green (495-570 nm), and blue (450-495 nm) wavelengths can be used, such as Nitride, Lutetium Aluminum Garnet, and $Ca_2PO_4Cl:Eu^{2+}$, respectively.

A difficult aspect to overcome is a lack of blue light emission in contrast to conventional LED white lights. While violet light can be combined with other colors to create white, it has been found that differences in perception from person to person exist for violet light. This means different people see a combined light differently; some might see too much violet, while others might see not enough violet; causing a misrepresentation of the color of white light overall. In addition, without enough blue light it is more difficult to achieve a high CRI. Previous attempts have utilized blue LEDs mixed with the other colors to boost CRI and balance the color of the mixed light output. Even with this approach some people still see the light differently depending on their sensitivity, but it has shown reduced differentiation of observed color overall of combined spectrums. Some embodiments herein instead add blue light through the use of phosphors, optical brighteners, or other blue emitting materials. These materials can absorb violet light and emit blue light, without the use of a discrete blue LED. Some phosphor material compositions include Yttrium Aluminum Garnet, Lutetium Aluminum Garnet, Nitride, Oxynitride, Calcium Sulfide, $Ca_2PO_4Cl:Eu^{2+}$, and Silicate. Some optical brightening agents are chemical derivatives of stilbene, coumarin, 1,3 diphenyl pyrazoline, naphthalene dicarboxylic acid, heterocyclic dicarboxylic acid, and cinnamic acid.

Figure 16:
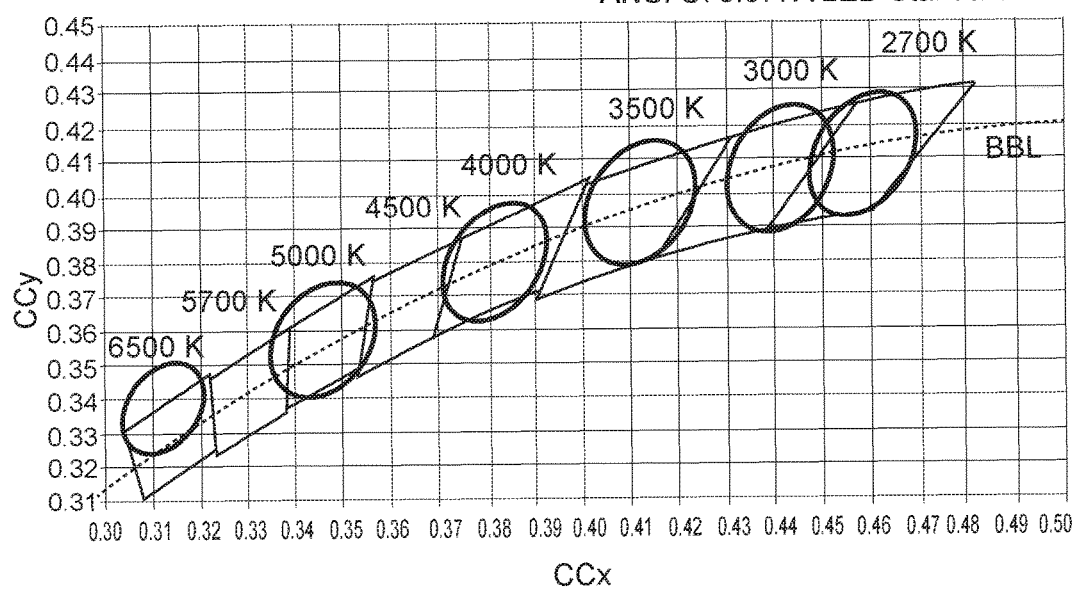
FIG. 16 illustrates an ANSI C78.377A LED Standards with accepted x-y coordinates at selected CCTs that are color coordinate ranges for light-emitting devices in some embodiments of the disclosure.

FIG. 16 serves as an example of color coordinates and ranges of color coordinates that could be achieved in practice in some embodiments of the disclosure. It should be understood that these are examples of some existing standards of color coordinates that can be achieved; other standards that exist or may be developed in the future for white light may be used. Additionally, the disclosed device may be approximately matched in color coordinates to CIE standard illuminants and/or standard illuminant families; it should be noted that the disclosed device may not match all defined characteristics of a standard illuminant, but in some embodiments will approximately match the xy color coordinates. Some of these additional CIE standard illuminants include but are not limited to A, B, C, D50, D55, D65, D75, E, F1, F2, F3, F4, F5, F6, F7, F8, F9, F10, F11, and F12.

The foregoing description of various aspects of the disclosure has been presented for the purpose of illustration and description. It is not intended to be exhaustive or to limit the disclosure to the precise form disclosed, and obviously, many modifications and variations are possible. Such variations and modifications that may be apparent to one skilled in the art are intended to be included within the scope of the present disclosure as defined by the accompanying claims.

What is claimed:

1. A light emitting device which inactivates microorganisms, the light emitting device comprising:
   one or more light emitters configured to emit light with a same wavelength in the range of 380 nm to 420 nm; and
   at least two light-converting materials arranged to convert a portion of light emitted from the one or more light emitters to at least two different wavelengths different from a wavelength of the light emitted from the one or more light emitters,
   wherein the light emitted from the one or more light emitters and the light emitted from the at least two light-converting materials mixes to form a combined light, the combined light being white, having a color rendering index (CRI) value of at least 70 and having a proportion of spectral energy measured in a 380 nm to 420 nm wavelength range of greater than 20%.

2. The light emitting device of claim 1, wherein at least one of the one or more light emitters comprises a light-emitting diode (LED).

3. The light emitting device of claim 1, wherein at least one of the one or more light emitters comprises a laser.

4. The light emitting device of claim 1, wherein at least one of the at least two light-converting materials includes at least one phosphor.

5. The light emitting device of claim 1, wherein at least one of the at least two light-converting materials includes at least one optical brightener.

6. The light emitting device of claim 1, wherein the combined light has a peak wavelength in the range of 380 nm to 420 nm.

7. The light emitting device of claim 1, wherein each of the one or more light emitters emits light having a peak wavelength of approximately 405 nm.

8. The light emitting device of claim 1, wherein the combined light has a CRI of at least 80.

9. The light emitting device of claim 1, wherein the one or more light emitters includes an array of light emitters and the at least two light-converting materials are evenly distributed over each light emitter of the array.

10. The light emitting device of claim 1, wherein the combined light has a correlated color temperature (CCT) between approximately 2,500 K and 5,000 K.

11. The light emitting device of claim 1, wherein the combined light has a proportion of spectral energy measured in a 380 nm to 420 nm wavelength range of greater than 30%.

12. The light emitting device of claim 1, wherein the combined light has a proportion of spectral energy measured in a 380 nm to 420 nm wavelength range of greater than 40%.

13. A light emitting device which inactivates microorganisms, the light emitting device comprising:
    one or more light emitters configured to emit a first light within a same wavelength in a range of 380 nm to 420 nm; and
    at least two light-converting materials arranged to be in a direct path of the first light, a first light-converting material configured to emit a second light in response to the first light being incident on the first light-converting material, and a second light-converting material configured to emit a third light in response to one or both of the first and second lights being incident on the second light-converting material,
    wherein the first light exiting the light emitting device, the second light exiting the light emitting device and the third light exiting the light emitting device mix to form a combined light, the combined light being white and having a color rendering index (CRI) value of at least 70,
    wherein the first light-converting material includes at least one optical brightener which emits light in the wavelength range of 450 nm to 495 nm,
    wherein the second light-converting material includes at least one phosphor which emits light in the wavelength range greater than 495 nm, and
    wherein the combined light has a proportion of spectral energy measured in a 380 nm to 420 nm wavelength range of greater than 20%.

14. The light emitting device of claim 13, wherein at least one of the one or more light emitters comprises a light-emitting diode (LED).

15. The light emitting device of claim 13, wherein the combined light has a peak wavelength in the range of 380 nm to 420 nm.

16. The light emitting device of claim 13, wherein the second light-converting material includes a first phosphor that emits light in the wavelength range of 620 nm to 750 nm, and a second phosphor that emits light in the wavelength range of 495 nm to 570 nm.

17. The light emitting device of claim 13, wherein the combined light has a CRI of at least 80.

18. The light emitting device of claim 13, wherein the combined light has a correlated color temperature (CCT) between approximately 2,500 K and 5,000 K.

19. The light emitting device of claim 13, wherein the one or more light emitters includes an array of light emitters and the at least two light-converting materials are evenly distributed over each light emitter of the array.

20. A light emitting device which inactivates microorganisms, the light emitting device comprising:
    a light emitter; and
    at least one light-converting material arranged to convert at least a portion of light emitted from the light emitter,
    wherein any light emitted from the light emitter and the at least a portion of converted light emitted from the at least one light-converting material mixes to form a combined light, the combined light being white, having a color rendering index (CRI) value of at least 70, having a correlated color temperature (CCT) between approximately 2,500 K and 5,000 K, and having a proportion of spectral energy measured in an approximately 380 nm to approximately 420 nm wavelength range of greater than approximately 20%.

* * * * *